US008740826B2

(12) United States Patent
Leismer

(10) Patent No.: US 8,740,826 B2
(45) Date of Patent: Jun. 3, 2014

(54) MUSCULOSKELETAL LOADING DEVICE

(76) Inventor: Jeffrey M. Leismer, Sheboygan, WI (US)

( * ) Notice: Subject to any disclaimer, the term of this patent is extended or adjusted under 35 U.S.C. 154(b) by 1093 days.

(21) Appl. No.: 12/658,903

(22) Filed: Feb. 16, 2010

(65) Prior Publication Data

US 2010/0222722 A1 Sep. 2, 2010

Related U.S. Application Data

(63) Continuation of application No. 11/433,988, filed on May 15, 2006, now Pat. No. 7,662,115, which is a continuation of application No. 10/419,005, filed on Apr. 18, 2003, now abandoned.

(60) Provisional application No. 60/373,546, filed on Apr. 18, 2002.

(51) Int. Cl.
*A61H 1/00* (2006.01)
*A61F 5/00* (2006.01)

(52) U.S. Cl.
USPC .................................. 601/49; 601/70; 601/79

(58) Field of Classification Search
USPC ............ 601/5, 23, 30, 33–35, 46, 49, 69–71, 601/78–79, 40; 602/20, 23, 25, 32, 36; 606/57–58
See application file for complete search history.

(56) References Cited

U.S. PATENT DOCUMENTS 2,058,563 A * 10/1936 Campbell ...................... 601/33
2,114,322 A 4/1938 Shafer
3,550,585 A * 12/1970 Howard et al. .................. 601/5
4,055,169 A 10/1977 Baker et al.
4,846,461 A 7/1989 Robards, Jr. et al.
4,875,469 A * 10/1989 Brook et al. ................... 601/40

(Continued)

FOREIGN PATENT DOCUMENTS

EP 0482988 4/1992
FR 2726184 5/1996

OTHER PUBLICATIONS

Qin et al., Nonlinear Dependence of Loading Intensity and Cycle Number in the Maintenance of Bone Mass and Morphology, Journal of Orthopaedic Research, 1998, 8 pages numbered 482-489, vol. 16, No. 4, Orthopaedic Research Society.

(Continued)

*Primary Examiner* — Justine Yu
*Assistant Examiner* — Christopher Miller
(74) *Attorney, Agent, or Firm* — Thomas D. Wilhelm; Wilhelm Law, S.C.

(57) ABSTRACT

A device for non-invasively mechanically stimulating bone or muscle includes a vibrational energy generator for applying vibrational energy to a first end of a length of a tissue which includes bone and/or muscle. The vibrational energy is for inducing strain in at least one region within the length of tissue. A restraint is disposed opposite the first end of the length to resist translation of the length during operation of the device and to provide loading to the bone or muscle. A connecting structure couples the restraint to the vibrational energy generator. The device does not require gravity to operate and as a result is expected to have applications in space, such as with astronauts, with those having bone aliments such as bed-ridden patients, persons with osteoporosis or disuse atrophy, athletes, recovering bone cancer patients, and persons with musculoskeletal disorders.

16 Claims, 10 Drawing Sheets

(56) References Cited

U.S. PATENT DOCUMENTS

| | | | | | |
|---|---|---|---|---|---|
| 5,052,375 | A | * | 10/1991 | Stark et al. | 601/34 |
| 5,052,378 | A | | 10/1991 | Chitwood | |
| 5,098,040 | A | | 3/1992 | Retat | |
| 5,178,137 | A | * | 1/1993 | Goor et al. | 601/40 |
| 5,451,202 | A | | 9/1995 | Miller et al. | |
| 5,484,388 | A | * | 1/1996 | Bassett et al. | 601/27 |
| 5,865,770 | A | * | 2/1999 | Schectman | 601/23 |
| 6,061,597 | A | | 5/2000 | Rieman et al. | |
| 6,106,490 | A | | 8/2000 | Shaw | |
| 6,379,393 | B1 | * | 4/2002 | Mavroidis et al. | 623/25 |

OTHER PUBLICATIONS

Rubin et al., Low mechanical signals strengthen long bones, Macmillan Magazines Ltd., Aug. 2001, 2 pages numbered 603-604, vol. 412.

Rubin et al., Mechanical Strain, Induced Noninvasively in the High-frequency Domain, Is Anabolic to Cancellous Bone, But Not Cortical Bone, Elsevier Science Inc., Mar. 2002, 8 pages numbered 445-452, vol. 30, No. 3.

* cited by examiner

MUSCULOSKELETAL LOADING DEVICE

CROSS REFERENCE TO RELATED APPLICATION

The present application is a continuation of U.S. patent application Ser. No. 11/433,988, filed May 15, 2006, which is a continuation of U.S. patent application Ser. No. 10/419,005, filed Apr. 18, 2003, which claims the benefit of U.S. provisional patent application No. 60/373,546 filed on Apr. 18, 2002, the entireties of each of the preceding applications being incorporated herein by reference in their entireties.

STATEMENT REGARDING FEDERALLY SPONSORED RESEARCH

This invention was made with United States Government support from the National Institute of Health through Grant No. 1R15HL67787-01. The United States Government has certain rights in this invention.

FIELD OF INVENTION

This invention relates generally to non-invasive musculoskeletal loading devices which provide adjustable loading.

BACKGROUND OF THE INVENTION

The health of human bones is of enormous importance. Bones provide support and protection for the human body. Osteoporosis is a disease characterized by low bone mass and structural deterioration of bone tissue which can seriously impede the ability of osteoporotic bones to provide support and protection for the body. An increased risk of bone fracture is present in individuals with osteoporosis. In 1995 alone, the cost of treatment for osteoporotic bone fractures was $13.8 billion. Around 28 million American's suffer from low bone mass or osteoporosis and are at risk of adding to the yearly cost of treatment for the disease. One in every 2 women and 1 in every 8 men over the age of 50 will develop a fracture in their lifetime due to the disease. With changing demographics and the aging of America, the significance of this national as well as international concern will only increase.

Bone disuse atrophy is a disease that can also lead to osteoporosis. While undergoing long flights in space, astronauts suffer from a lack of weight bearing on their bones. Bone disuse atrophy has been seen to cause decreases in bone mass from 1-2% per month in astronauts. Decreases in bone mass of this magnitude could seriously impede an astronaut's bone health during long duration space flight, such as what will someday be incurred by astronauts on roundtrip missions to Mars or other planets. With the closest medical assistance for an astronaut being millions of miles away, it is of key importance that an astronaut's bones do not degrade to a point where they risk fracture during missions.

The majority of current countermeasures for bone disuse atrophy are not entirely effective. Mineral and hormone treatments have been administered as attempts to maintain bone mass, but have had little benefit in the long run. Mechanical stimulation of bone has been shown to achieve the goal of maintaining bone mass and structure. However, some methods of applying mechanical stimuli may be more damaging than good, while others may only partially aid in the maintenance of bone strength.

Recent research involving the effects of vibrational bone loading have proved successful at increasing bone density in sheep. This and related research have utilized a vibrating platform upon which the sheep or other subject stands. Because this arrangement relies on gravity, the arrangement does not provide an adjustable load and loses its effectiveness as gravity is reduced.

SUMMARY

A device for non-invasively mechanically stimulating bone or muscle includes a vibrational energy generator for applying vibrational energy to a first end of a length of a tissue which includes bone and/or muscle. The vibrational energy is for inducing strain in at least one region within the length of the tissue. A restraint is disposed opposite the first end of the length to resist translation of the tissue length or the device during operation of the device, and to provide compressive or tensile loading to the bone or muscle. The restraint can be disposed on a variety of bodily regions, including the knee, waist and shoulder.

A connecting structure couples the restraint across the tissue to be treated. The device does not require gravity to operate and as a result is expected to have applications in space, such as with astronauts, with those having bone ailments such as bed-ridden patients, persons with osteoporosis or disuse atrophy, athletes, recovering bone cancer patients, and persons with musculoskeletal disorders.

The level or frequency of the vibrational energy applied can be adjustable. The length of the connecting structure also can include structure for adjustment, wherein shortening the length provides compression and lengthening the length provides tension to the tissue region. The connecting structure can include a sensor for measuring a level of applied compression or tension.

The vibrational energy generator can comprise an adjustable cam driven by a motor. A speed controller is preferably provided and connected to the motor for controlling a speed of the motor. The arrangement provides an adjustable frequency spectrum output by the vibrational energy generator. The motor can drive a follower plate.

The connecting structure can comprise a plurality of structures which are each disposed circumferentially along a volume which includes the tissue length. The plurality of structures can be activatable independently, wherein activation of some but not all of the plurality of structures provides circumferential compression which varies as a function of angular position along at least a portion of the tissue length being treated.

A gravity-independent method for non-invasively mechanically stimulating bone or muscle, includes the steps of restraining a tissue region of a subject comprising at least one of bone and muscle, and applying vibrational energy through the region to induce strain in the region. The method can include the step of imposing a compressive or tensile force on the region during the applying step. The magnitude of the compressive or tensile force can be adjustable.

The method can be performed in a substantially weightless environment, such as space. The method can also be performed on earth, such as applied to supine subjects as no gravity is required to practice the claimed method.

The method can include the step of providing a vibrational energy generator, wherein a frequency spectrum provided by the vibrational energy generator is adjustable. The method can be applied to only a portion of the subject thus providing site-specific treatment. The frequency of vibrational energy can be 20, 30, 40, 50, 60, 70, 80, 90, 100 Hz, or other frequencies.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

Figure 1:
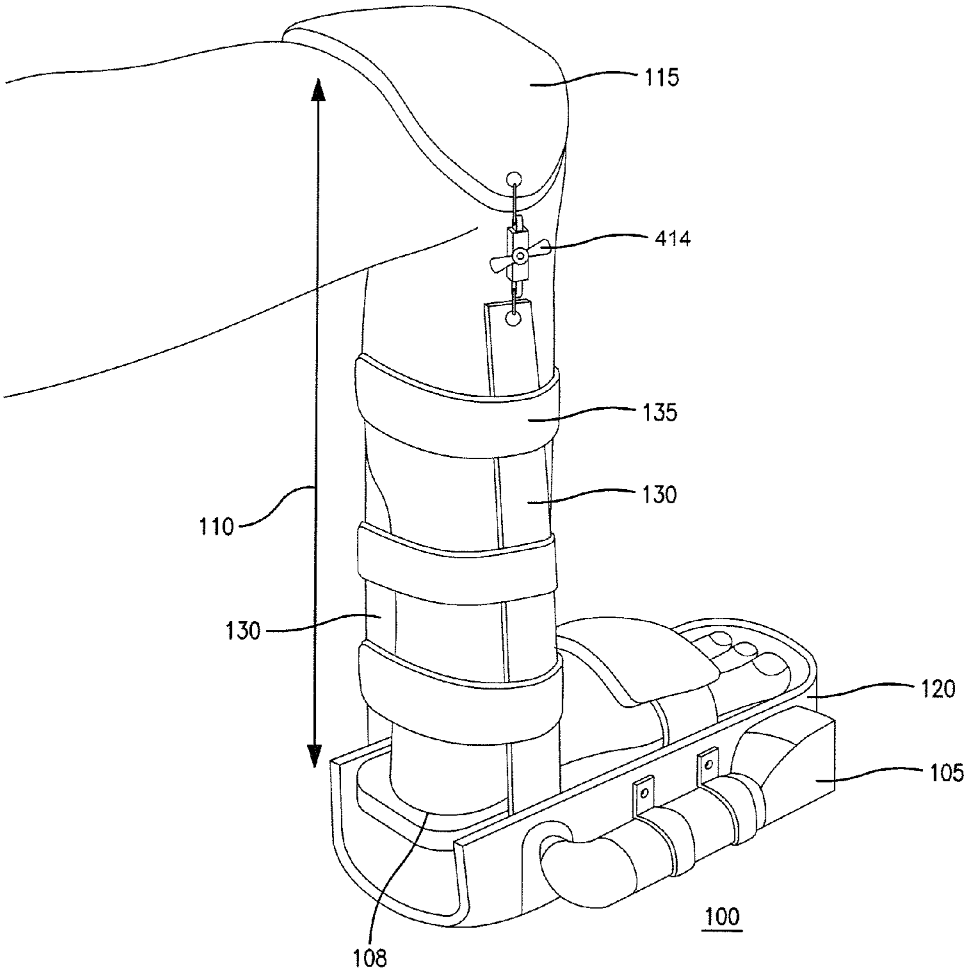
FIG. 1 illustrates an exemplary bone loading device, according to an embodiment of the invention.

FIG. 1 illustrates a device 100 for non-invasively mechanically stimulating bone or muscle in a subject, according to an embodiment of the invention. Device 100 can be used to mechanically stimulate an osteogenic effect in bone or the development of muscle. Device 100 includes a vibrational energy generator 105 for applying vibrational energy to a first end 108 of a length of a tissue to be treated 110 which includes bone and/or muscle therein (not shown). The vibrational energy is for inducing strain in at least one region within the length of the tissue 110.

A restraint 115 is disposed opposite the first end of the length 110 to resist translation of the length during operation of the device 100. Restraint 115 is coupled to connecting structure 130 which couples restraint 115 to the first end of the length of tissue to be treated, such as through connection to frame 120. Connecting structure 130 also provides a compressional coupling force and localized tensile forces to the region to be treated, the force preferably being adjustable, such as through variation of its length. Straps 135, such as Velcro® straps (or equivalent) are preferably provided for securing the connecting structure 130 to the length of tissue to be treated 110.

Unlike earlier vibrational loading devices, device 100 does not require gravity to operate and can be used in microgravity environments (e.g. space) or by supine (e.g. bedridden) individuals on earth. For vibrational treatment, bodily regions must have some coupling force (e.g. compression or tension) acting on them in order for the vibrational energy to transfer through the targeted region. On earth, a person capable of standing upright can utilize their body weight to provide the coupling force to permit vibrational energy to transfer through their body. However, for the gravity reliant systems while in space, when the first vibrational oscillation is applied, the subject would be sent adrift by the vibrational forces because no forces would be holding the vibration inducing device to the person. In contrast, connecting structure 130, through its connection across a of length of the tissue to be treated 110, provides both a coupling and restraining force which does not depend on gravity.

Another advantage provided by device 100 is the ability to treat discrete portions (site-specific treatment) of a subject, rather than the entire subject being treated when the individual stands on a vibrational plate. Thus, conventional vibrational loading devices gravitationally load the subject from head to toe, or from a seated position the spine of the subject is loaded. In contrast, device 100 can treat a single discrete tissue length, such as tissue length 110 disposed between the knee and foot of an individual.

Although connecting structure 130 shown in FIG. 1 physically connects across the length of the tissue to be treated 110 to provide a load, physical connection is not required. Loading can also be provided using an electromagnetic attractive force to induce compressive loading, such as using an electrical or magnetic field. For example, restraint 115 and a portion of frame 120 can each be electrodes which if biased with opposite polarities, will produce an attractive force which can provide a compressive load across tissue length 110.

Figure 2:
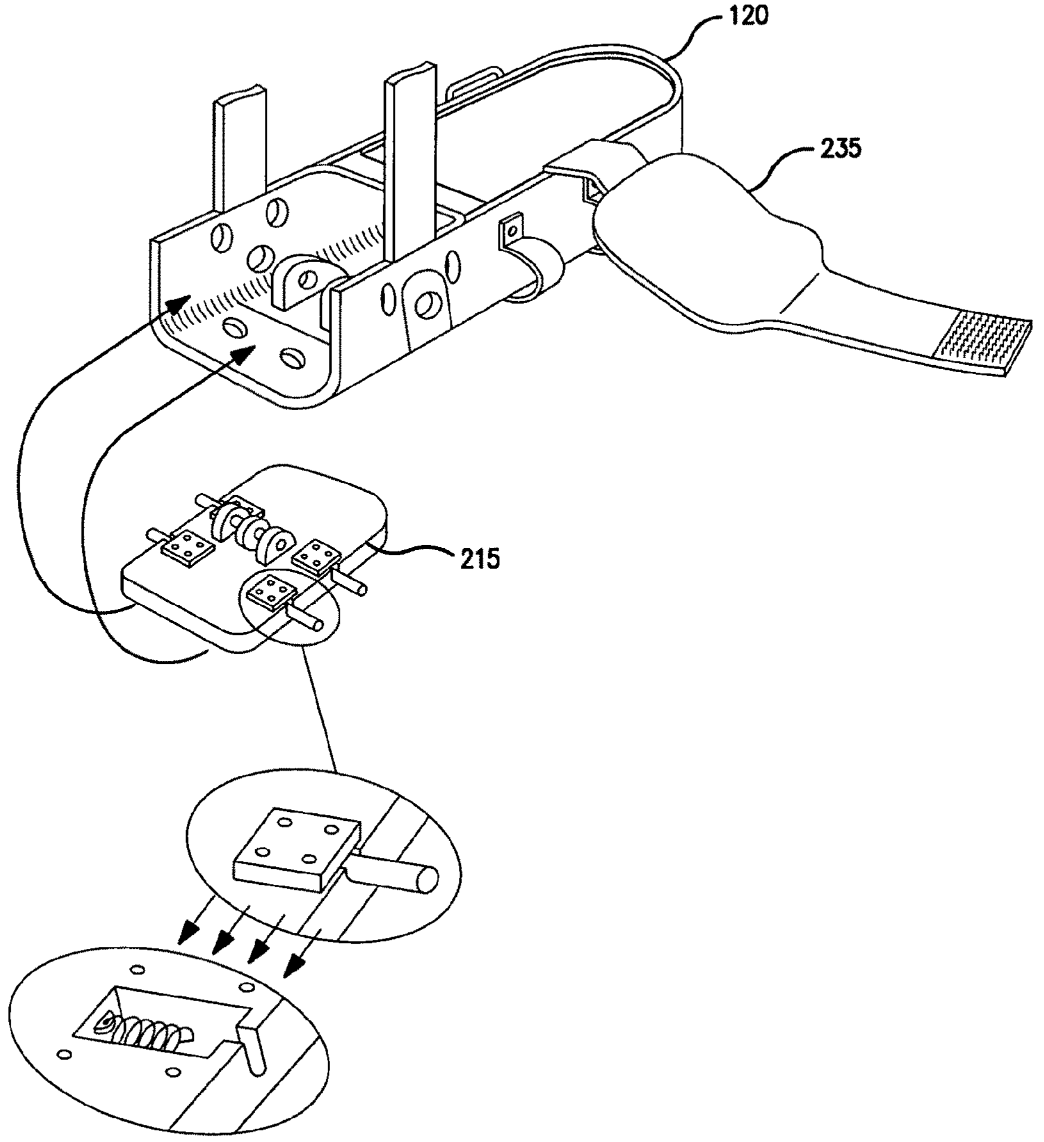
FIG. 2 shows an exemplary embodiment of a frame, according to an embodiment of the invention.

FIG. 2 shows an exemplary embodiment of frame 120 with vibrational energy generator 105 removed. Frame 120 includes a follower plate 215 upon which the first end 108 of a length of tissue to be treated 110 is placed upon during operation of the device. However, those having ordinary skill in the art will realize that loading can be applied by structures other than follower plate 215. Optional strap 235 can be included to further secure the first end 108 of a length of tissue to be treated 110 to frame 120. In operation, follower plate 215 is vibrated up and down by a suitable driving structure.

Figure 3:
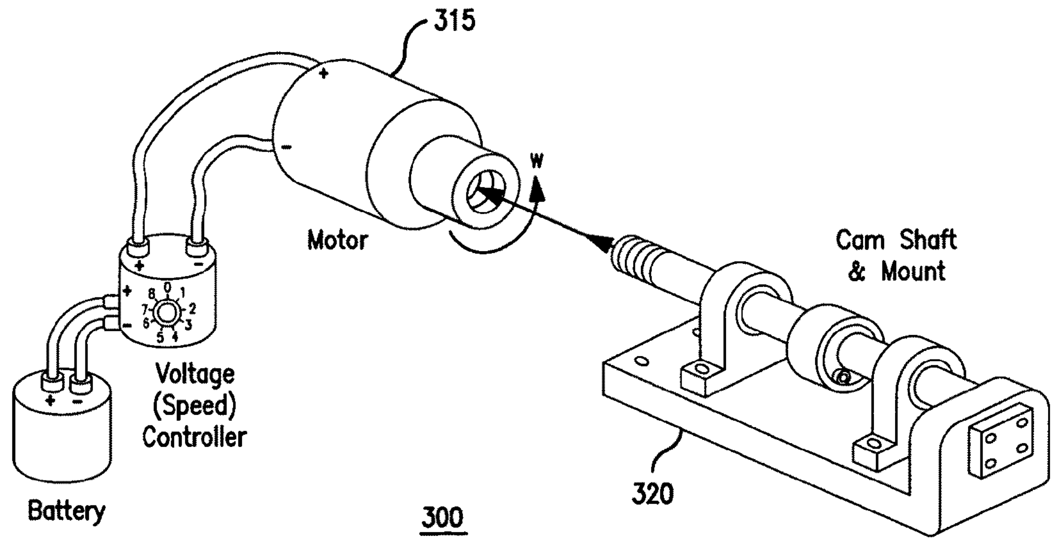
FIG. 3 shows a driving structure which comprises a motor to induce motion in a cam-follower which couples to a follower plate to apply vibrations to a subject, according to an embodiment of the invention.

In one embodiment shown in FIG. 3, vibrational energy to drive follower plate 215 can be produced via driving structure 300 which comprises a motor 315 to induce motion in a cam-follower 320 which couples to follower plate (not shown in FIG. 3). Such cam-type vibrational device will produce sinusoidal vibrational patterns. Although not shown, electromagnetic linear actuators and other vibrational energy sources can also be used with the invention. Rotation of motor 315 inherently rotates the cam shaft. Rotation of the cam shaft inherently rotates the cam. The tension in connecting structures 130 inherently applies a force tending to hold the lower end of the tissue 110, being treated, in contact with the cam follower, which urges the cam follower into contact with the cam. Thus, while tissue is being treated, there is a constant linkage between the drive motor, which provides the energy for the vibration activity, and the surface of the cam follower which delivers the vibration activity to the tissue being treated. Applied to tissue 110 shown in FIG. 1, the mechanical vibrations at the follower plate will transfer the vibrations from the heel or ball of the subject's foot through tissue length 110.

Figure 7:
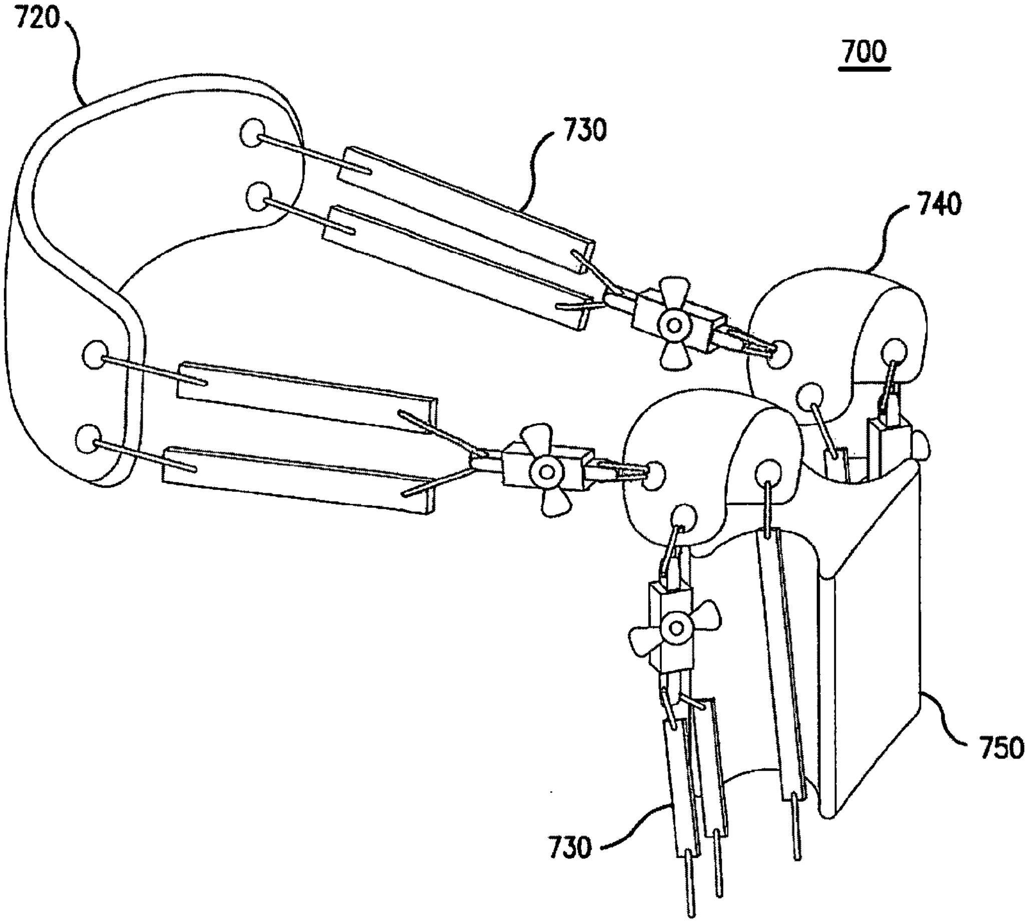
FIG. 7 shows a restraint for use in connection with the bone loading device of FIG. 1.
Figure 8:
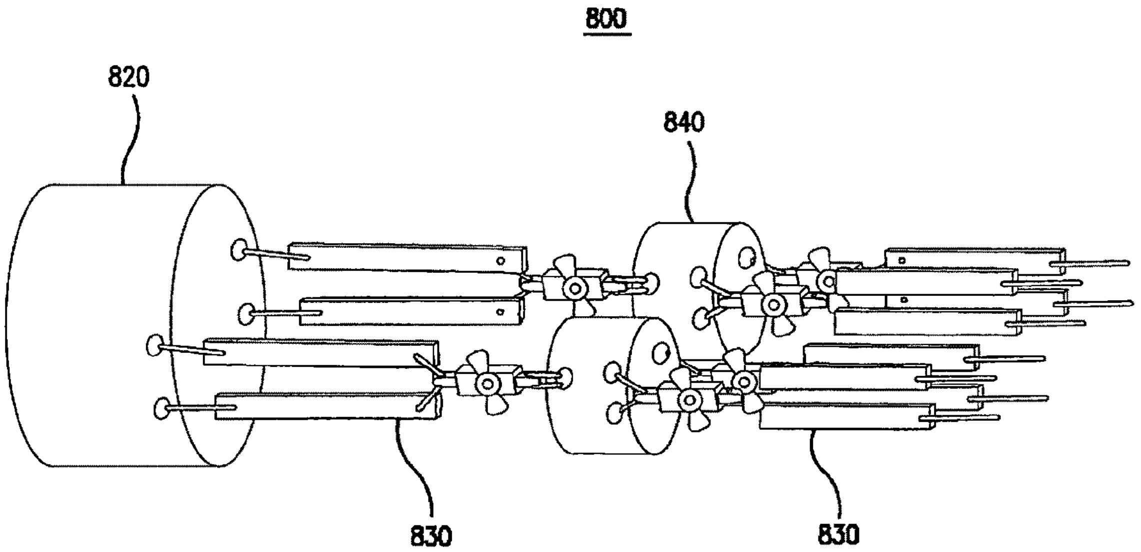
FIG. 8 shows an alternative embodiment of a restraint for use in connection with the bone loading device of FIG. 1.

Although described generally as for treating the region of the tissue between the knee and the foot, the invention is in no way limited in this way. Those having ordinary skill in the art will realize a variety of other regions, such as the knee, waist, shoulder, arms and spine can be treated using device 100. In fact as illustrated in FIG. 7, a back restraint 700 with a lower back coupling pad 720, connecting structures 730, knee coupling pads 740 and leg pad 750 is shown as one example of a restraint for use in connection with the device 100. This embodiment of a restraint provides two non-invasive points of coupling at the back and the knees. To provide another alternative restraint for use in connection with device 100, FIG. 8 shows a waist restraint 800 having a waist restraint pad 820, connecting structures 830 and knee coupling pads 840.

Figure 4:
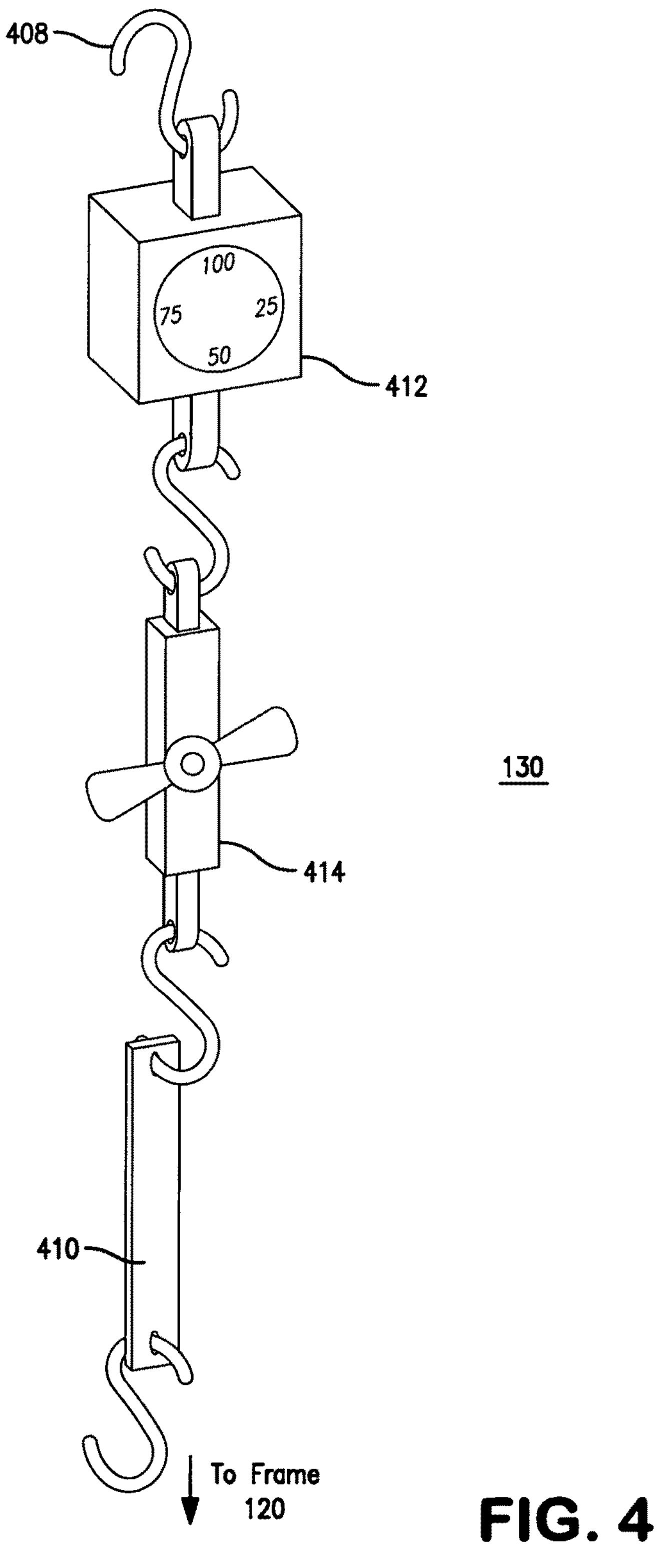
FIG. 4 shows an exemplary connecting structure, according to an embodiment of the invention.

FIG. 4 shows an exemplary connecting structure 130. Connecting structure 130 includes a fastener 408 to connect to restraint 115. Fastener 408 can be coupled to an optional force sensor 412. Force sensor 412 is shown coupled to adjustable knob 414 which is attached to a bar 410. Bar 410 connects to frame 120 (not shown). Adjustable knob 414 can increase or decrease the length of connecting structure 130 to provide adjustable levels of compressive or localized tensile loading. Although not shown, electronic controls can be integrated with connecting structure 130 to provide automatic coupling force adjustments.

Adjustability of device 100 is thus provided by connecting structure 130 shown in FIG. 4 as it is capable of providing a compressive or localized tensile force capable of variation. As used herein, the applied force is also referred to as a preload. The preload, when present, acts on the targeted tissue region, such as a region of bone. A preload acting on a targeted bone region can be used to induce larger strains and to more effectively control the directions of strains in the bones or muscles of a subject as compared to applied vibrations alone.

Although not shown, device 100 can also include one or more strain gauges to monitor the strain induced along tissue length 110, such as disposed on the skin of a subject. Together with a conventional feedback and control system, the level of preload and/or vibrational energy parameters applied by vibrational energy generator 105 can be dynamically adjusted to provide a desired level of strain.

By providing larger strains to targeted tissue regions using preloads according to the invention, the time required for therapy to achieve a desired level of bone (or muscle) strengthening may be reduced. In particular, the addition of preloads acting on bones can produce larger strains at the midshaft of the diaphysis of long bones because of the curved shape of long bones. Thus, the use of preloads with the loading device 100 increases the efficacy of the process of increasing bone (or muscle) strength.

Figure 5A:
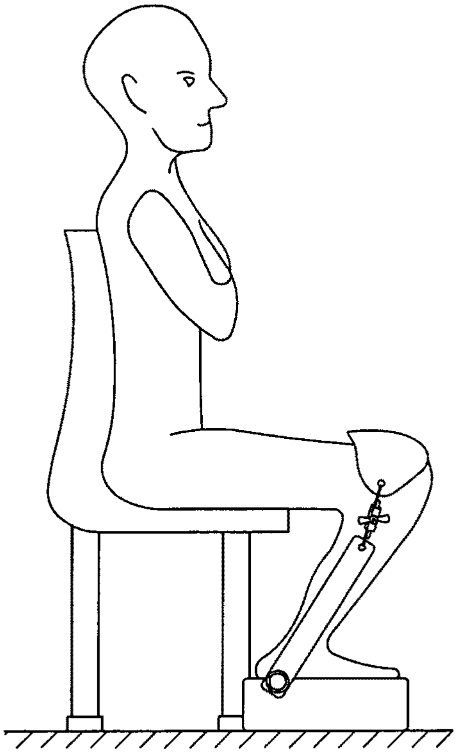
FIGS. 5(*a*) and (*b*) show therapy applied at two different knee angles using the invention.
Figure 5B:
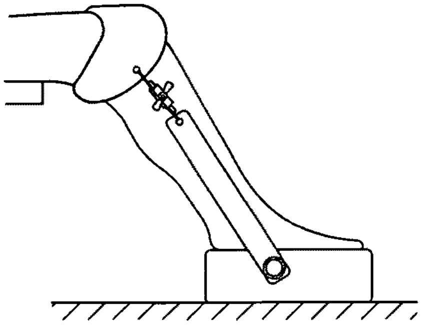

Further treatment adjustability provided by device 100 results from the ability to operate the device when the foot (or other tissue length) is flexed at different angles. FIGS. 5(*a*) and (*b*) show therapy being applied using device 100 at two different knee angles. FIG. 5(*a*) shows a minimum muscle stretch on the posterior side of the lower leg, while FIG. 5(*b*) shows a maximum muscle stretch of the same region. The maximum muscle stretch shown in FIG. 5 (*b*) provides enhanced therapy in the calf region. An alternative embodiment includes active adjustment of the tissue length flexure during therapy to better stimulate gravitational forces acting on the body during activities such as walking.

Figure 6A:
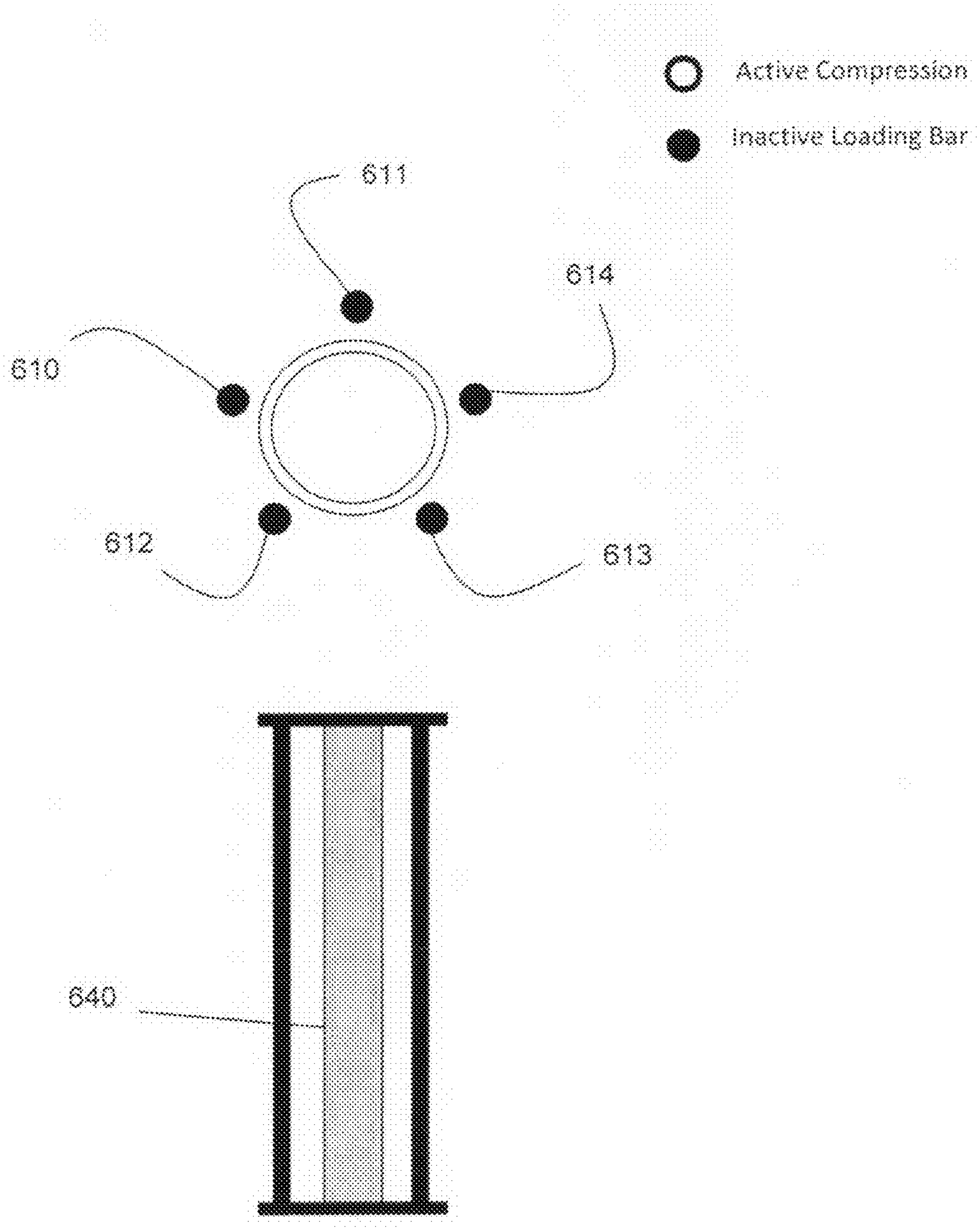
FIGS. 6(*a*), 6(*b*), and 6(*c*) show an alternative connecting structure which comprises a plurality of separate compression-loading units, according to yet another embodiment of the invention.
Figure 6B:
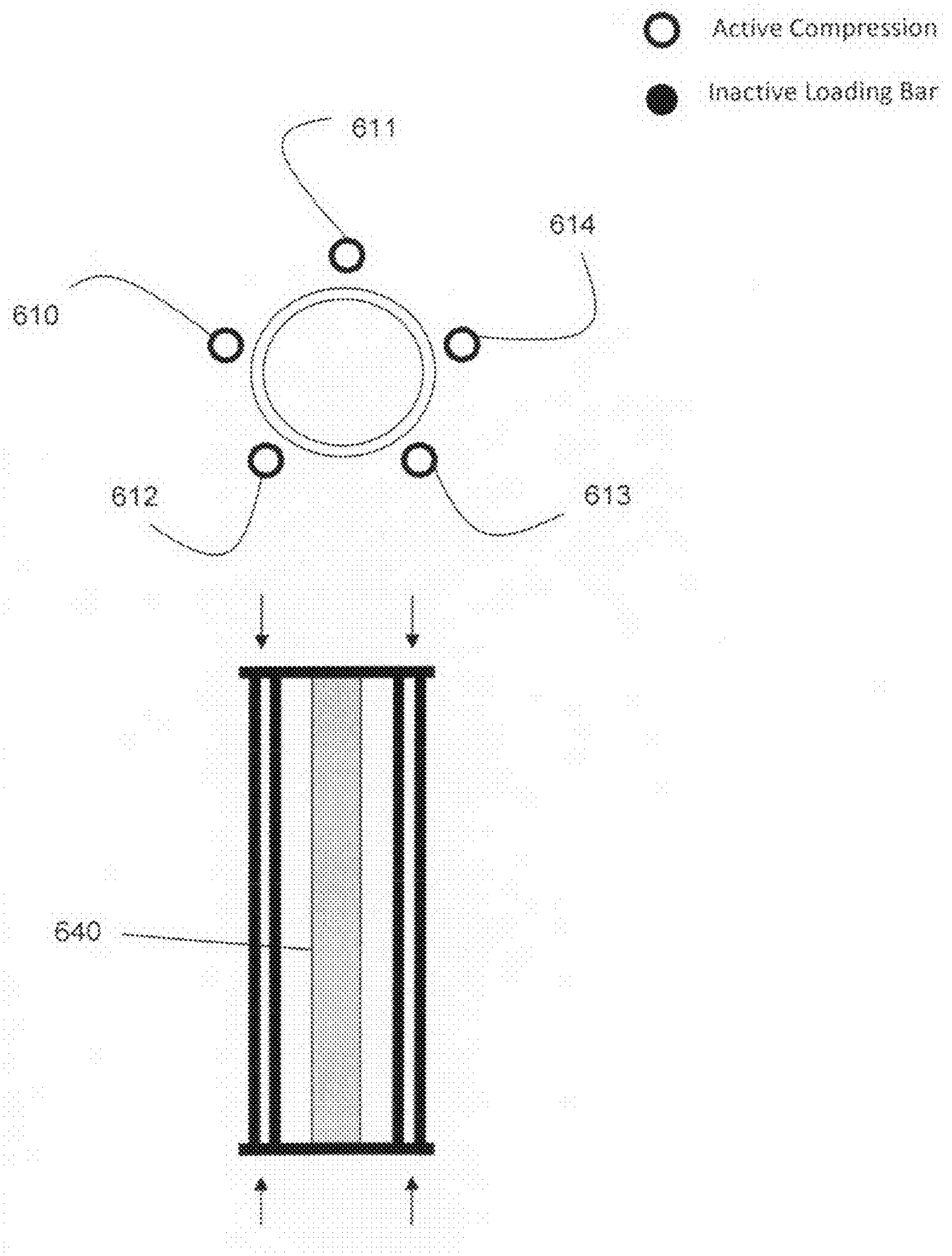
Figure 6C:
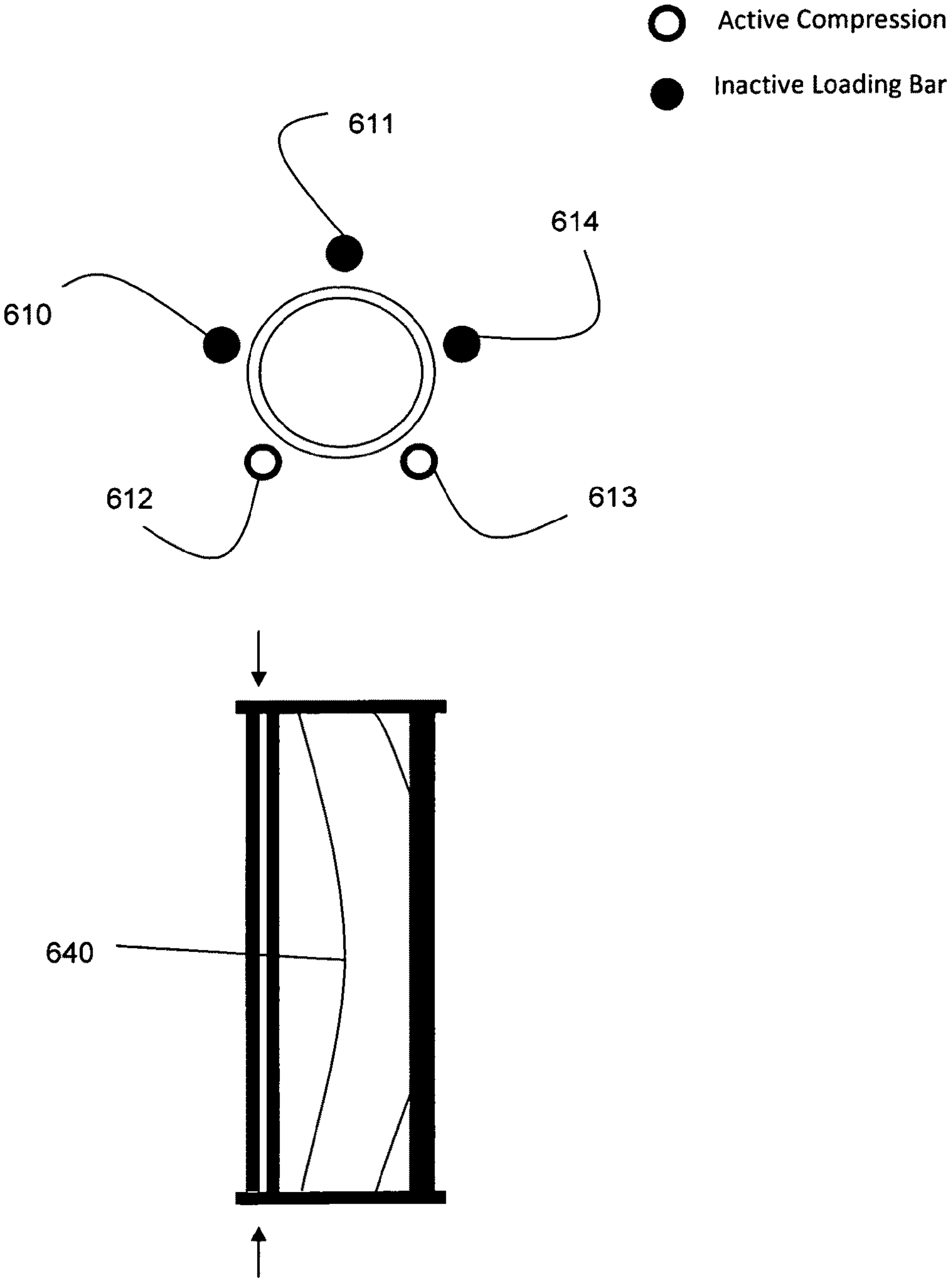

In another embodiment of the invention, preloads can be directed through specific circumferential positions. FIGS. 6(*a*), 6(*b*), and 6(*c*) show connecting structure 600 adapted to provide preloads directed through specific circumferential positions. Rather than using two (2) connecting structures shown in FIG. 1, with each connecting structure covering only a small percentage of the circumference of tissue length 110, devices according to the invention can include a plurality of connecting structures which collectively each cover a portion of an arc length spanning substantially the entire circumference of tissue length 110. This embodiment can induce equal or unequal stress or strain along the entire tissue length being treated.

For simplicity, FIGS. 6(*a*), 6(*b*), and 6(*c*) show an alternative connecting structure which comprises a plurality of separate connecting structures, referred to in this embodiment as force-loading units 610-614. Force-loading units 610-614 are placed circumferentially around a bodily region to be treated 640. Each force loading unit 610-614 is disposed between restraint 630 and frame 620 and preferably includes an adjustment knob or other structure (not shown) to independently increase or decrease their respective lengths to provide adjustable levels of compressive or localized tensile loading.

Loading units 610-614 can be activated one-by-one or in multiple succession to apply bending, tensile, and/or compression loads to target bone (or muscle) regions 640. This permits key regions of bone to be strengthened as a function of angular position.

The top depictions in FIGS. 6(*a*)-(*c*) represent cross-sections of a long bone 640, while the pictures at the bottom show a lateral view of the same bone 640. FIG. 6(*a*) depicts bone 640 subject to no compressive load. FIG. 6(*b*) depicts bone 640 subject to uniform compression since all the compressional-loading units are actively providing the same level of compression. The arrows shown indicate the direction of loading. FIG. 6(*c*) depicts bone 640 subject to site-specific circumferential loading. Here, force-loading units 612 and 613 are actively applying compression, while force-loading units 610, 611 and 614 are inactive (not applying compression). Loading bone 640 as shown in FIG. 6(*c*) created a bending moment about the bone, thus circumferentially influencing bone morphology.

This method of loading bone can be advantageous particularly when one side of a bone is weaker that another. The location where stresses in a bone are the highest generally are the sites where bone adaptations are most necessary, so that new bone will be deposited most readily. Therefore loading a bone such that bending is induced will allow new bone to be deposited more readily at the site where additional support is necessary.

By actively changing the circumferential loading direction during vibration-induced bone strengthening sessions, the bone 640 will be subjected to loading in multiple directions, which may prove advantageous to uniaxial loading (i.e., compression loading alone). Preferential stiffness of a bone loaded uniaxially can cause deleterious effects if the bone is later subjected to loading in shear. This is because the bone is only geared to absorb loading in the direction it has been "trained" to absorb loads in.

The invention has many potential uses. For example, U.S. Pat. No. 6,061,597 to Reiman et al discloses a method and device for healing bone fracture. The invention can likely be used to enhance the healing bone fracture through coupling of vibrational energy through the region is healing. Thus, using the present invention, bone can experience increased mass, density, and structural strength, while muscle can experience increased strength, size, flexibility. Joints/ligaments/tendons can also benefit from the invention and receive increased flexibility. Skin toning is also possible using the invention.

While the preferred embodiments of the invention have been illustrated and described, it will be clear that the invention is not so limited. Numerous modifications, changes, variations, substitutions and equivalents will occur to those skilled in the art without departing from the spirit and scope of the present invention.

I claim:

1. A method of non-invasively stimulating a length of tissue of a living body, the length of tissue including bone tissue and muscle tissue, thereby treating both the bone tissue and the muscle tissue, the method comprising:

(a) connecting a treatment device to the body proximate the length of tissue to be treated, the treatment device comprising (i) a first restraint, (ii) a second restraint, (iii) a connecting structure comprising a plurality of connectors, the connecting structure being adapted and configured to provide a connection between the first restraint and the second restraint and to apply a tensile force between the first and second restraints, whereby the tensile force on the connecting structure results in a preload compressive force on the length of tissue to be treated, the tissue to be treated comprising at least one bone segments, and (iv) a vibration energy generator secured in the device, the connecting of the treatment device to the body including:

applying the first restraint at a first location on the body relative to the length of tissue to be treated, applying the second restraint at a second different location on the body relative to the length of tissue to be treated, the first restraint being connected to the second restraint through the connecting structure, and thereby applying the preload compressive force to the length of tissue to be treated;

(b) activating the vibration energy generator and thereby applying vibration energy to the body and along the length of tissue to be treated and thereby treating the length of tissue to be treated; and (c) changing the circumferential loading direction of the connecting structure by adjusting one or more, but less than all, of the connectors while applying the vibration energy treatment.

2. The method as in claim 1, wherein the first and second restraints and the connecting structure, collectively, span a first bone segment and a second bone segment, across a bone joint, the method further comprising translating the at least one connector, thereby pivoting the first bone segment relative to the second bone segment, across the joint while applying vibration energy to the bone segments being treated, the application of vibration energy to the bone segments effecting adjustment of the lengths of bone tissue in the bone segments being treated, and correspondingly adjusting the length of muscle tissue being treated.

3. The method as in claim 2, comprising translating the at least one connector while applying the vibration energy.

4. The method as in claim 1, the connecting structure comprising at least first and second connectors, the method further comprising adjusting a length of one or more of the connectors selectively so as to create a bending moment about the at least one bone segment.

5. The method as in claim 1, the connecting structure comprising at least first, second, and third connectors, the method comprising the activating of one or more of the connectors selectively so as to create a bending moment about the at least one bone segment.

6. The method as in claim 1, the method further comprising, while applying the vibration energy treatment, adjusting at least one of (i) the preload level in the at least one connector, or (ii) the level of the vibration energy being applied by the vibration energy generator, or (iii) location of at least one such connector.

7. The method as in claim 1, the method further comprising applying the preload across a joint, and while applying the vibration energy treatment, adjusting a length of a muscle tissue being treated.

8. The method as in claim 1, the method further comprising, while applying the vibration energy, adjusting the preload.

9. The method as in claim 8, the adjusting of the preload comprising adjusting a length of the connecting structure.

10. The method as in claim 8, the adjusting of the preload comprising adjusting the magnitude of the preload.

11. The method as in claim 8 comprising adjusting the preload by translating an end of one of the connecting structures.

12. The method as in claim 8, the adjusting of the pre-load comprising selectively applying pre-load force to one or more of the connectors so as to create a bending moment between first and second ends of the at least one bone segment.

13. The method as in claim 1, the at least one bone segment comprising at least a first bone segment and a second bone segment, and a joint between the first and second bone segments, the method further comprising adjusting at least one, but not all, of the connectors and thereby selectively loading the joint spanned by the connectors.

14. The method as in claim 8, further comprising pivoting the first bone segment relative to the second bone segment while applying the vibration energy, the pivoting of the first bone segment relative to the second bone segment correspondingly adjusting the length of the muscle tissue which is being treated.

15. A method of non-invasively stimulating a length of tissue of a living body, the length of tissue including bone tissue and muscle tissue, thereby treating both the bone tissue and the muscle tissue, the method comprising:

(a) connecting a treatment device to the body proximate the length of tissue to be treated, the treatment device comprising (i) a first restraint, (ii) a second restraint, (iii) a connecting structure comprising at least one connector, the connecting structure being adapted and configured to couple the first restraint to the second restraint, the at least one connector being adapted and configured to apply a tensile force between the first and second restraints, whereby the tensile force on the connecting structure results in a preload compressive force on the length of tissue to be treated, and (iv) a vibration energy generator secured in the device, the vibration energy generator being adapted and configured to apply vibration energy across the length of tissue to be treated, the connecting of the treatment device to the body including:

applying the first restraint at a first location on the body relative to the length of tissue to be treated, applying the second restraint at a second different location on the body relative to the length of tissue to be treated, and connecting the first restraint to the second restraint using the connecting structure, and thereby applying the preload compressive force to the length of tissue to be treated; and (b) activating the vibration energy generator and thereby applying vibration energy to the body and along the length of tissue to be treated and thereby treating the length of tissue to be treated, and (c) adjusting the preload on the connecting structure while applying the vibration energy to the tissue being treated.

16. A method of non-invasively stimulating a length of tissue of a living body, the length of tissue including bone tissue and muscle tissue, thereby treating both the bone tissue and the muscle tissue, the method comprising:

(a) connecting a treatment device to the body proximate the length of tissue to be treated, the treatment device comprising (i) a first restraint, (ii) a second restraint which interacts with the length of tissue to be treated, (iii) a connecting structure adapted and configured to provide a connection between the first restraint and the second restraint so as to apply a tensile force between the first and second restraints, whereby the tensile force on the connecting structure applies a preload compressive force on the length of tissue to be treated, (iv) a vibration energy generator secured in the device, the vibration energy generator being adapted and configured to generate vibration energy, and (v) a linkage between the vibration energy generator and the second restraint, the connecting of the treatment device to the body including applying the first restraint at a first location on the body relative to the length of tissue to be treated, applying the second restraint at a second different location on the body relative to the length of tissue to be treated, and the first restraint being connected to the second restraint using the connecting structure, the first and second restraints and the connecting structure collectively applying the preload compressive force to the length of tissue to be treated; and (b) activating the vibration energy generator and thereby applying vibration energy to the length of tissue being treated, the linkage between the driver which provides the energy for the vibration activity, and the second restraint, which delivers the vibration activity to the tissue being treated providing a constant connection between the driver and the second restraint while vibration energy is being applied to the tissue being treated.

* * * * *